United States Patent
Vitali et al.

(10) Patent No.: US 6,585,633 B2
(45) Date of Patent: *Jul. 1, 2003

(54) BRACHYTHERAPY SEED CARTRIDGE

(75) Inventors: Dario Vitali, Cincinnati, OH (US); Thomas J. Sierocuk, West Chester, OH (US); Kip M. Rupp, New Richmond, OH (US); Scott N. Barton, Loveland, OH (US); Michael A. Colbert, Cincinnati, OH (US); Gregory D. Bishop, West Chester, OH (US); David H. Ruder, Mason, OH (US)

(73) Assignee: C. R. Bard, Inc., Murray Hill, NJ (US)

( * ) Notice: Subject to any disclaimer, the term of this patent is extended or adjusted under 35 U.S.C. 154(b) by 8 days.

This patent is subject to a terminal disclaimer.

(21) Appl. No.: 09/779,993

(22) Filed: Feb. 9, 2001

(65) Prior Publication Data

US 2001/0008950 A1 Jul. 19, 2001

Related U.S. Application Data

(63) Continuation of application No. 09/359,867, filed on Jul. 26, 1999, now Pat. No. 6,267,718.

(51) Int. Cl.[7] .......................... A61M 29/02; A61N 5/00
(52) U.S. Cl. ............................................. 600/7
(58) Field of Search ................... 600/1–8; 604/97–100, 604/33, 57, 59, 60, 280, 283, 118, 533, 537, 539, 249

(56) References Cited

U.S. PATENT DOCUMENTS

| | | |
|---|---|---|
| 4,105,030 A | 8/1978 | Kercso |
| 4,207,797 A | 6/1980 | Gyorik |
| 4,396,021 A | 8/1983 | Baumgartner |
| 4,402,308 A | 9/1983 | Scott |

(List continued on next page.)

FOREIGN PATENT DOCUMENTS

| | | |
|---|---|---|
| AT | 390-884 B | 7/1990 |
| EP | B10 202 090 | 11/1986 |
| EP | B10299 004 | 3/1994 |
| EP | B1 0 321 176 | 2/1995 |
| JP | 04-64363 A | 12/1992 |
| WO | 97/22379 WO | 6/1997 |
| WO | 99/20337 WO | 4/1999 |

OTHER PUBLICATIONS

First experiences with interstitial brachycuria therapy (low dose rate I–125 seeds in carrier/Vicryl and high dose rate IR–192 afterloading system) in palliation of head and neck tumors W. Schwab[1], G. Reis[1], and K handschuh[1] HNO© 1986, magazine, pp. 34:3270333.

(List continued on next page.)

*Primary Examiner*—Samuel G. Gilbert
(74) *Attorney, Agent, or Firm*—Stroock & Stroock & Lavan LLP

(57) ABSTRACT

The present invention is directed to a seed cartridge assembly including a cartridge body, a seed drawer slideably disposed within the cartridge body, a radiation shield slideably disposed around the cartridge body and a seed retainer in the seed drawer. Further embodiments of the present invention include a seed cartridge assembly as described above including a gravity lock between the seed drawer and the cartridge body. Further embodiments of the present invention include a seed cartridge assembly as described above, wherein the cartridge body includes a magnification lens positioned above the seed drawer. Further embodiments of the present invention include a seed cartridge assembly as described above wherein a seed channel extends axially along the seed drawer and a plurality of vents extending from the seed channel to an exterior surface of the seed drawer. Further embodiments of the present invention include a seed cartridge assembly as described above wherein the gravity lock includes a moveable locking element, a first locking recess in an interior surface of the cartridge body and a second locking recess in an exterior surface of the drawer opposite the first locking recess.

20 Claims, 15 Drawing Sheets

U.S. PATENT DOCUMENTS

| | | | |
|---|---|---|---|
| 4,461,280 | A | 7/1984 | Baumgartner |
| 4,509,506 | A | 4/1985 | Windorski et al. |
| 4,539,981 | A | 9/1985 | Tunc |
| 4,550,449 | A | 11/1985 | Tunc |
| 4,597,753 | A | 7/1986 | Turley |
| 4,661,103 | A | 4/1987 | Harman |
| 4,671,280 | A | 6/1987 | Dorband et al. |
| 4,697,575 | A | 10/1987 | Horowitz |
| 4,754,745 | A | 7/1988 | Horowitz |
| 4,815,449 | A | 3/1989 | Horowitz |
| 4,820,267 | A | 4/1989 | Harman |
| 4,900,304 | A | 2/1990 | Fujioka et al. |
| 4,925,030 | A | 5/1990 | Ball |
| 4,968,317 | A | 11/1990 | Tormala et al. |
| 4,976,686 | A | 12/1990 | Ball et al. |
| 5,201,738 | A | 4/1993 | Scott et al. |
| 5,242,373 | A | 9/1993 | Scott et al. |
| 5,460,592 | A | 10/1995 | Langton et al. |
| 5,494,620 | A | 2/1996 | Liu et al. |
| 5,626,829 | A | 5/1997 | Koutrouvelis |
| 5,906,574 | A | 5/1999 | Kan |
| 5,928,130 | A | 7/1999 | Schmidt |
| 5,938,583 | A | 8/1999 | Grimm |
| 6,010,446 | A | 1/2000 | Grimm |
| 6,267,718 | B1 * | 7/2001 | Vitali et al. .................... 600/7 |

OTHER PUBLICATIONS

New Intraoperative Brachytherapy Techniques for Positive or Close Surgical Margins D. Nori, M.D., M. Bains, M.D., B.S. Hilaris, M.D., L. Harrison, M.D., D. Fass, M.D., T. Peretz, M.D., D. Donath, M.D. and Z Fuks, M.D., Department of Radiation Oncology, Surgery, University of Pennsylvania School of Medicine, Philadelphia, PA, USA Journal of Surgical Oncology pp. 42:54–59 Sep., 1989.

An Improved operative technique for placement of brachytherapy catheters in treatment of soft tissue sarcomas R. Alex HIS, Michael H. Torosian and Lawrence J. Solin Oncology Reports 3: 453–455, Mar. 1996.

Tissue Adhesive Versus Suture Wound Repair at 1 Year: Randomized Clinical Trial Correlating Early, 3–Month, and 1–Year Cosmetic Outcome James Quinn MD, George Wells, PhD, Terri Sutcliffe, BScN, Mario Jarmuske, MD, Jennifer Maw, MD, Ian Stiell, MD, MSc, Peter Johns, MD, Dec. 1998 32:6 Annals of Emergency Medicine, pp 645–649.

Inoperative Brachytherapy Following Thorascopic Wedge Resection of Stage 1 Lung Cancer Thomas A. d'Amato, MD. PhD; Michael Galloway, MD; Gary Szydlowski, MD; Alex Chen, MD; and Rodney J. Landreneau, MD, FFCP Clinical Investigators, Chest 1998; 114:1112–1115.

Iodine–125 Brachytherapy in the Treatment of Colorectal Andenocarcinoma Metastic to the Liver Rafael Martinez–Monge, MD, Subir Nag, MD, Carol A. Nieroda, MD, Edward W. Martin MD ©American Cancer Society 121801225, Mar. 1999.

Reduction of Radioactive Seed Emobilization to the LUNC Following Prostate Brachytherapy Elizabeth M. Tapen, MD, John C. Blasko, MD, Peter G. Grimm, DO, Haakon Ragde, MD, Pay Luse, MS, Stephanie Clifford, John Sylvester, MD, and Thomas W. Griffin, MD, Int. J. Radiation Oncology Biol. Phys. vol. 42, No. 5 pp. 1063–1067, Jul. 31, 1998.

Abstracts Presented for the Thirtieth Annual Meeting of the Society to Bynecologic Oncologists Hyatt Regency San Francisco, Embarcadero Center, San Francisco, California, Mar. 20–24, 1999, Gynecologic Oncology 72, 443–527 (1999).

A New Spacing Material for Interstitial Implantation of Radioactive Seeds J. Hammer, M.D>, R. Hawliczek, M.D., K.H. Karcher, M.D., and M. Riccabona, M.D., I.J. Radiation Onclology Biology Physics Mar. 1991, vol. 20 No. 3 pp. 621–625.

Scott Paryani Quick Seeder for Transperineal Prostate Implantation Walter P. Scott, MD, Shayam B. Paryani, MD, Michael M. Michaels, MD, John W. Wells, MD, Douglas W. Johnson, MD, Anand M. Kuruvilla, MD, Williams Cancer Center, Baptist Outpatient Center, Jacksonville, Florida Endocurietherapy/Hyperthermia Oncology 1993, 9:15–18.

Transparent Lead Acrylic Cartridge for Absorbable Radioactive Seed/Spacer Technique Walter P. Scott, MD, Charles Judson Williams Cancer Center, Jacsonville, FL 32207 Radiation Oncology Biology Physics, Aug. 1983, vol. 9, No. 8.

A New Device for Interstitial 125 Iodine Seed Implantation Robert Hawliczek, M.D.,[1] Joseph Neubauer, B.SC.,[2] Werner F.O. Schmidt, PH.D Peter Grunert, M.D.[3] and Lawrence R. Coia, M.D.[4].

Peroperative Brachytherapy with the Use of a Vicryl© Mat in Advanced or Recurrent Pelvic Tumors J.H. Meerwaldt*[a], th. Wiggers[b], A.G. Visser[c], A. Slot[d] Radiotherapy and Oncology 37 (1995) 167–169.

Intraoperative $^{125}$I Brachytherapy for High–Risk Stage 1 Non–Small Cell Lung Carcinoma Alex Chen, M.D., Michael Galloway, M.D. Rodney Landerneau, M.D., Thomas D'Amato, M.D., Ph.D. Athanasios Colonias, M.D., Stephen Karlovits, M.D., Annette Quinn, R.N., Tibetha Santucci, R.N., Shalom Kalnicki, M.D., and Douglas Brown, M.D. Department of Radiation Oncology and Thoracic Surgery, Allegheny General Hospital, Pittsburgh, PA Int. J. Radiation Oncology Biol. Phys. vol. 44, No. 5, pp. 1057–1063, 1999.

* cited by examiner

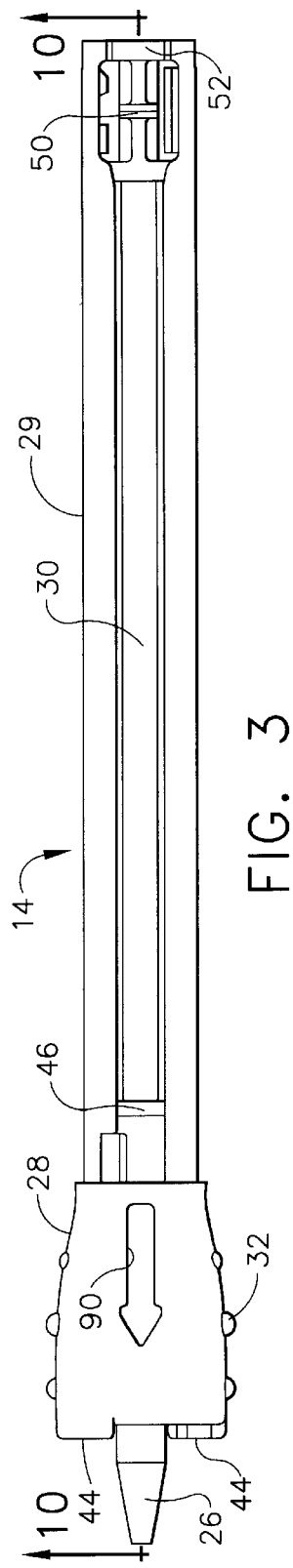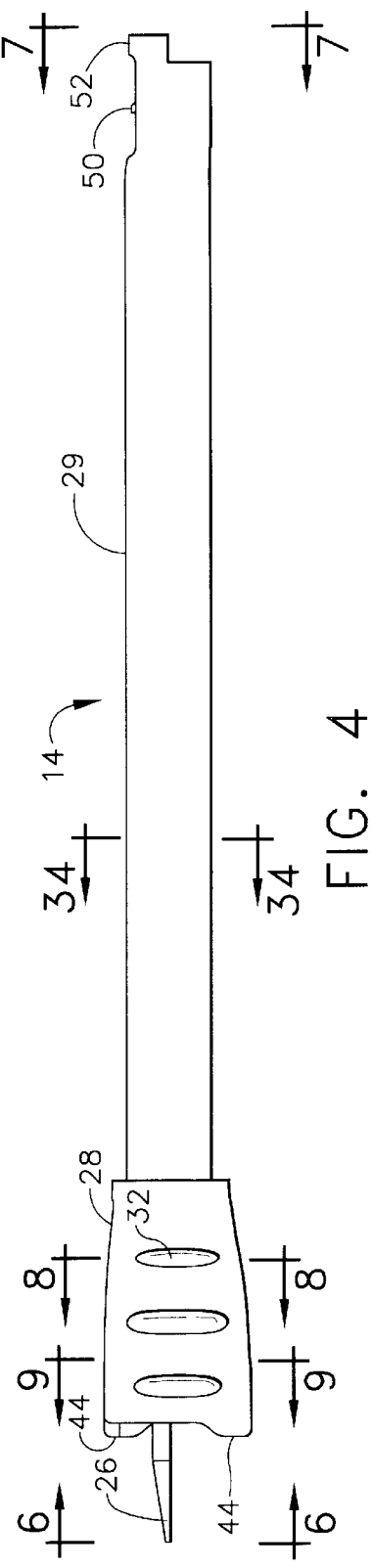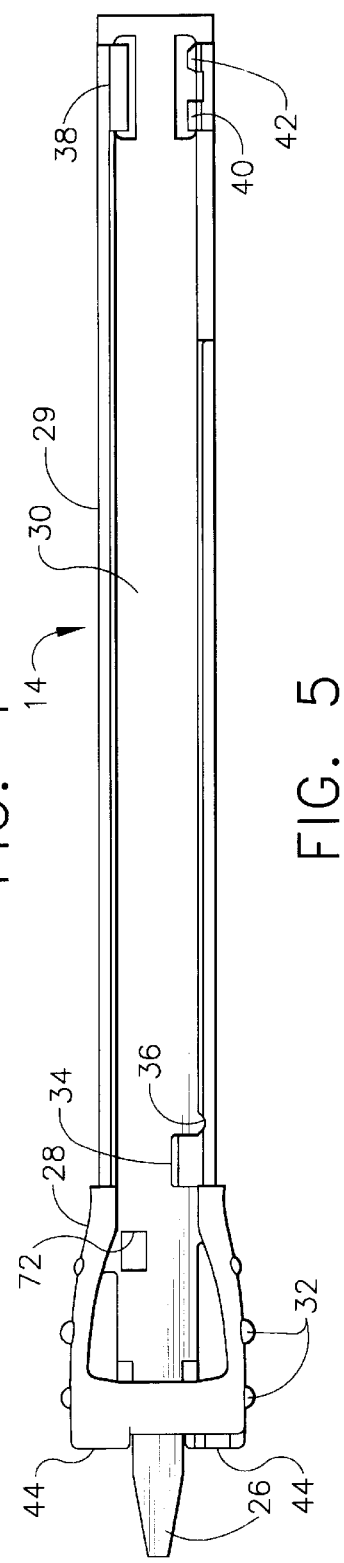

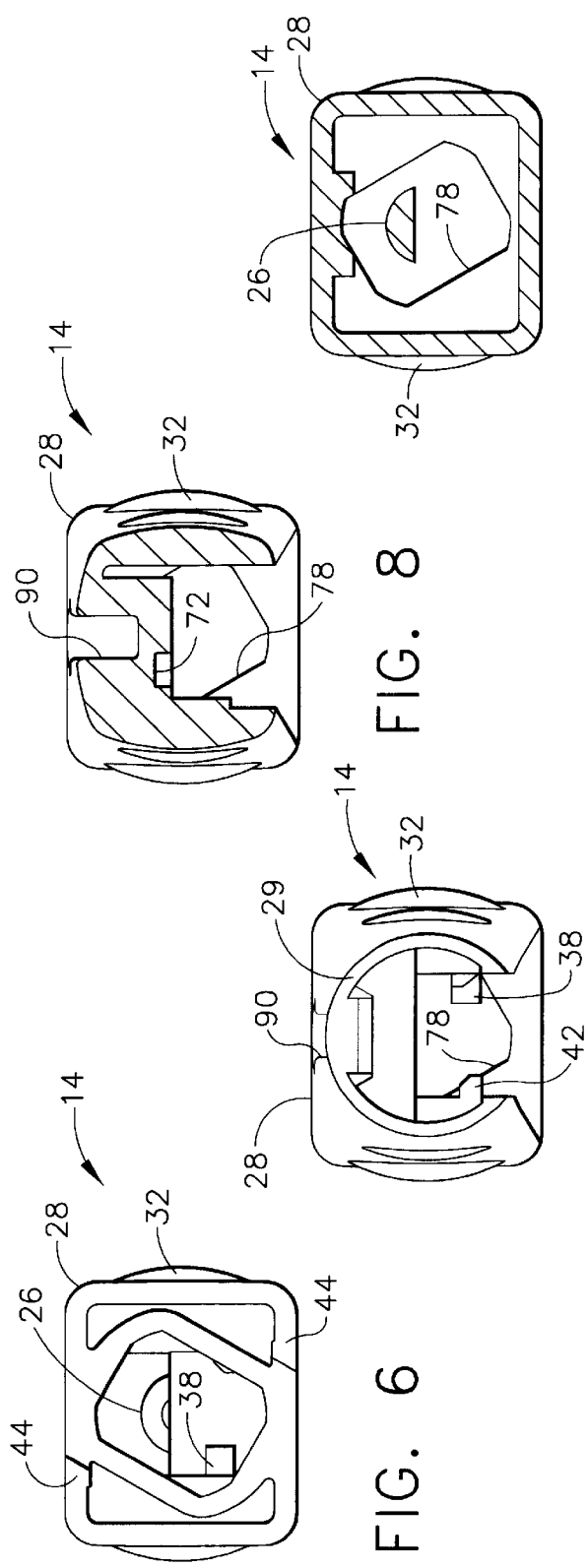

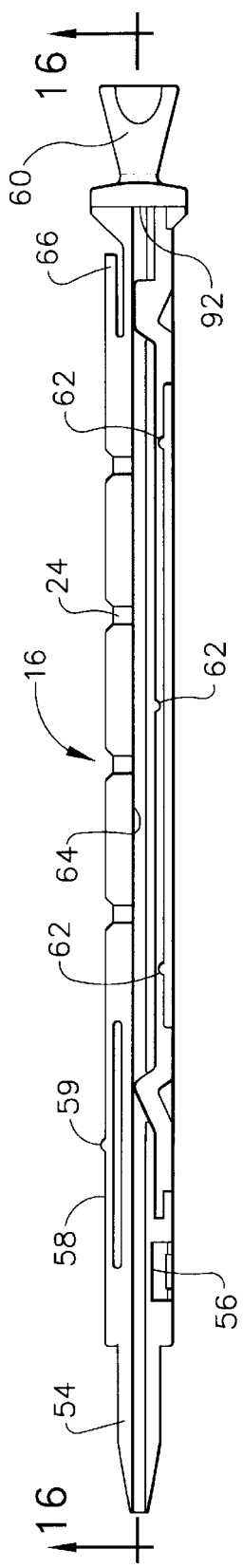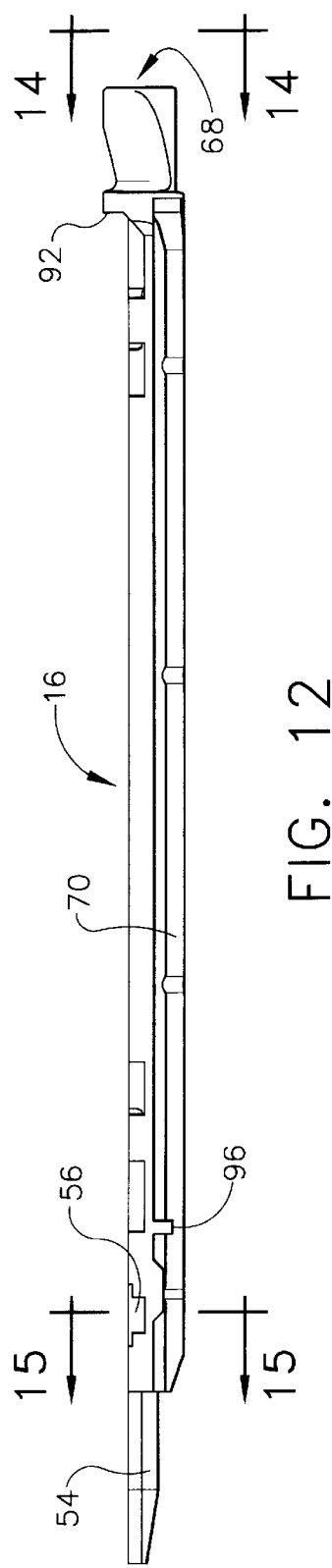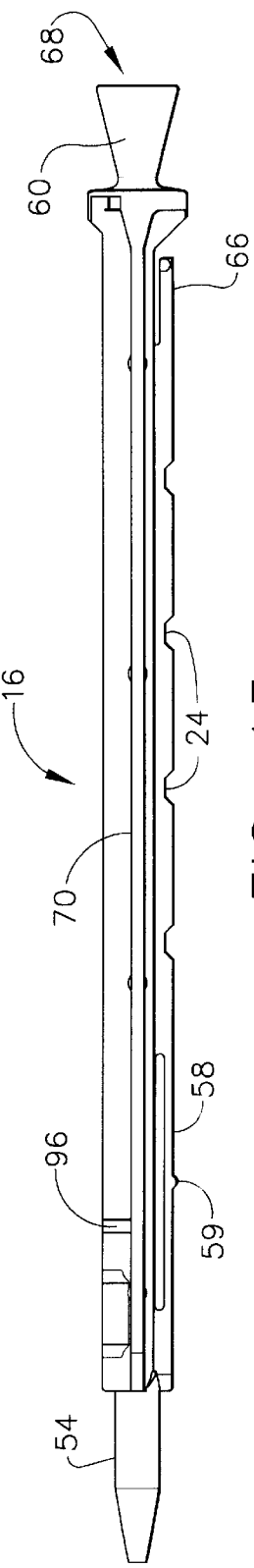

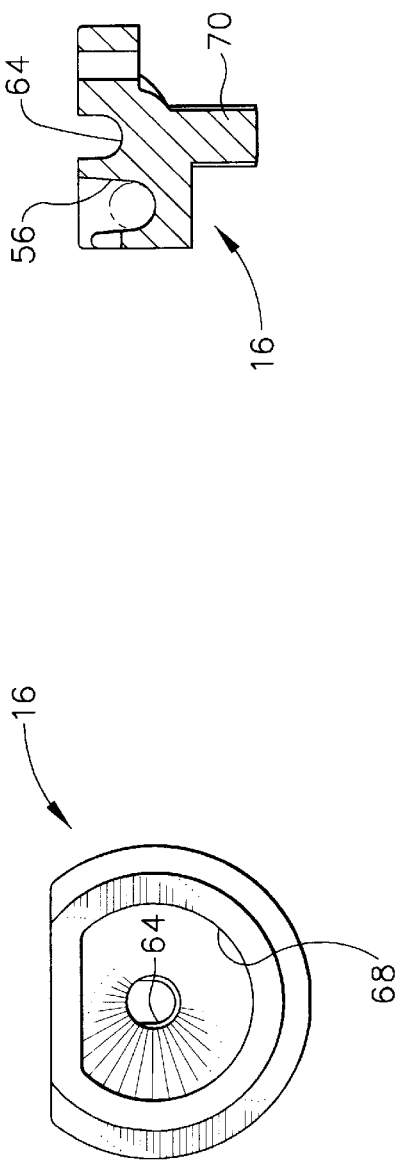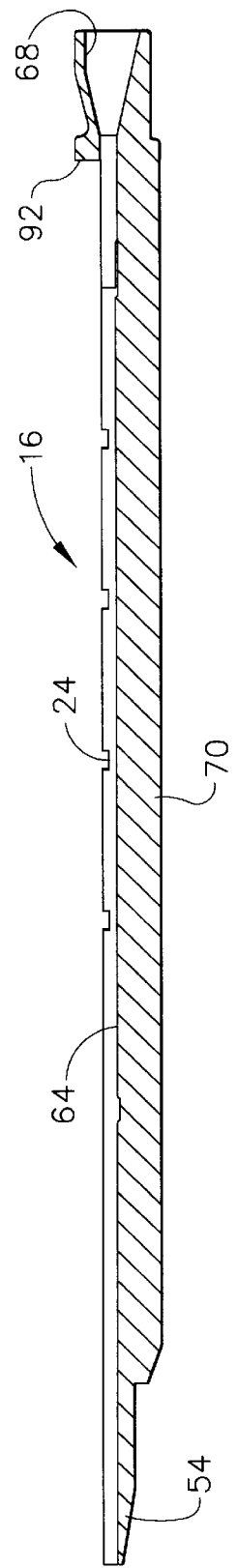

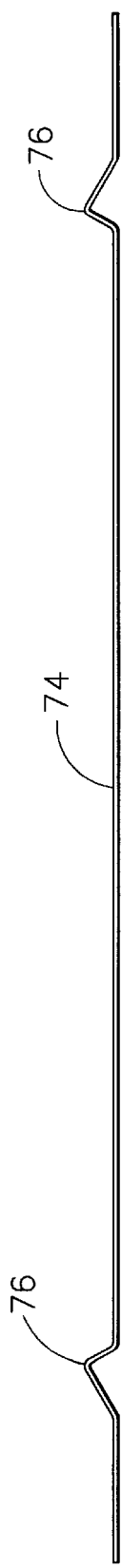
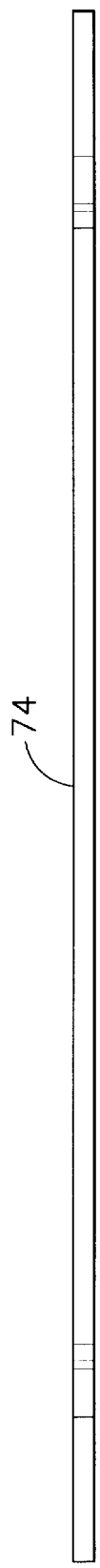
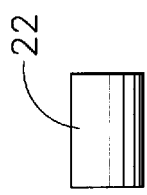
FIG. 20
FIG. 21
FIG. 22

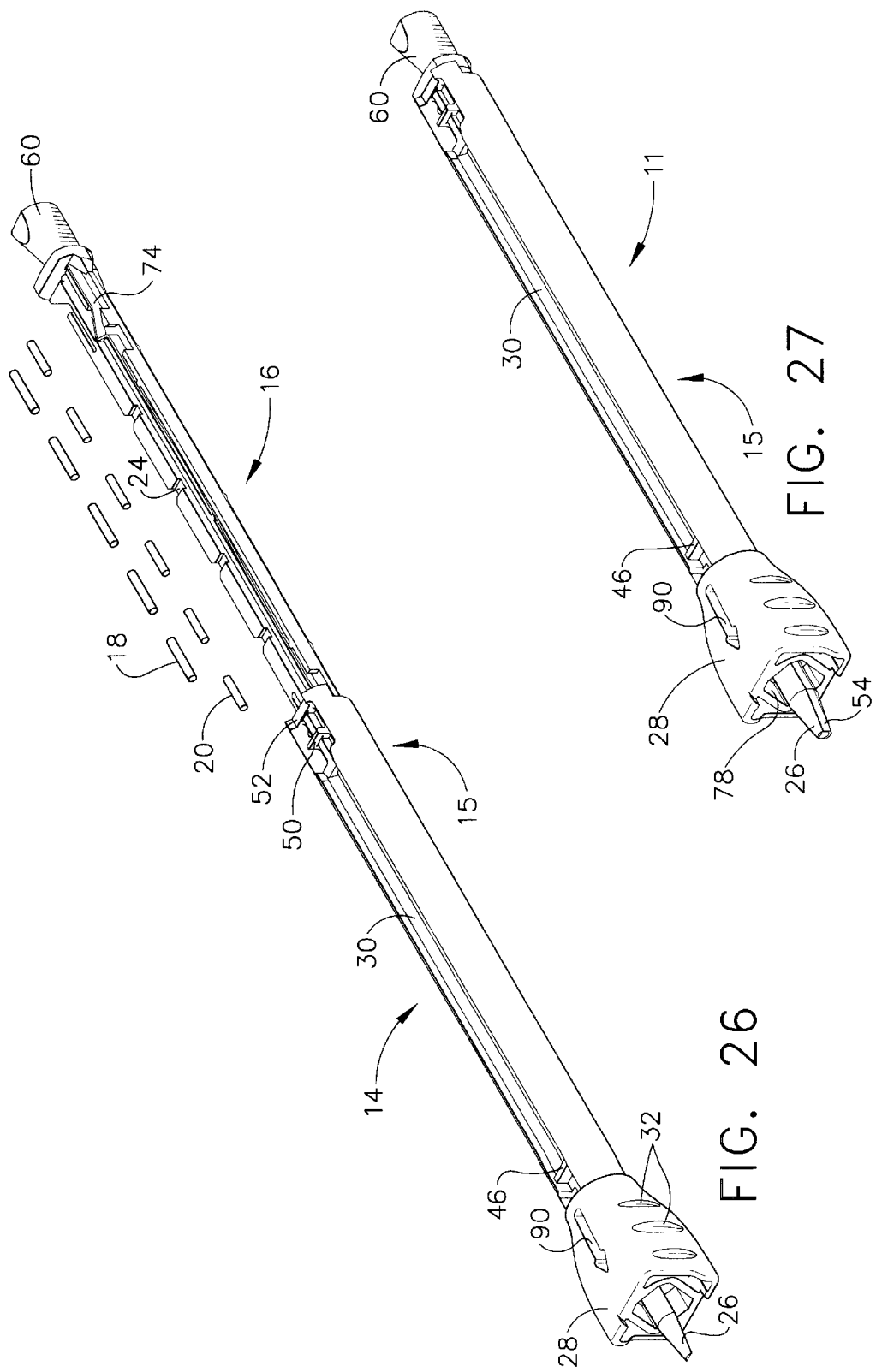

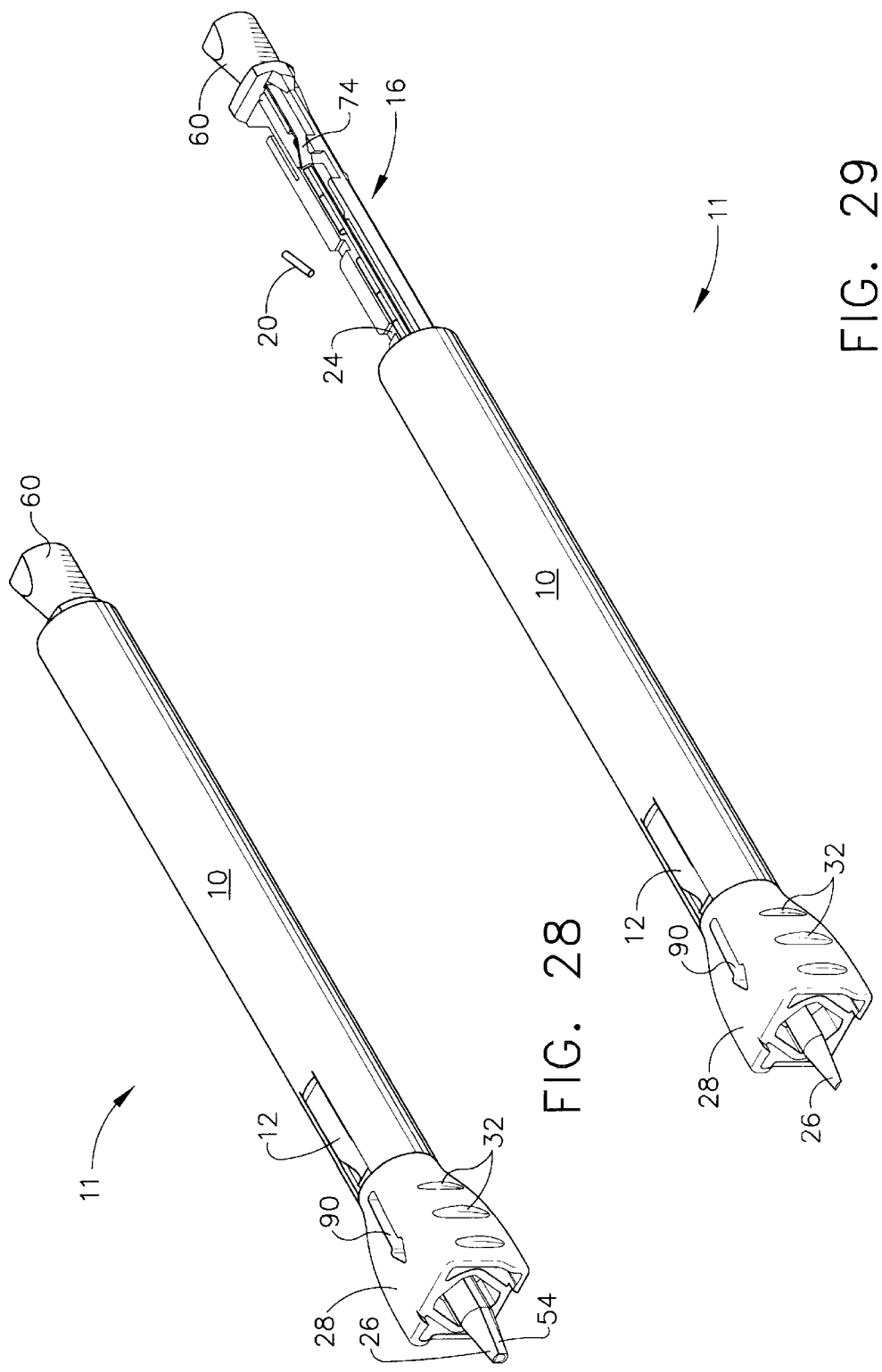

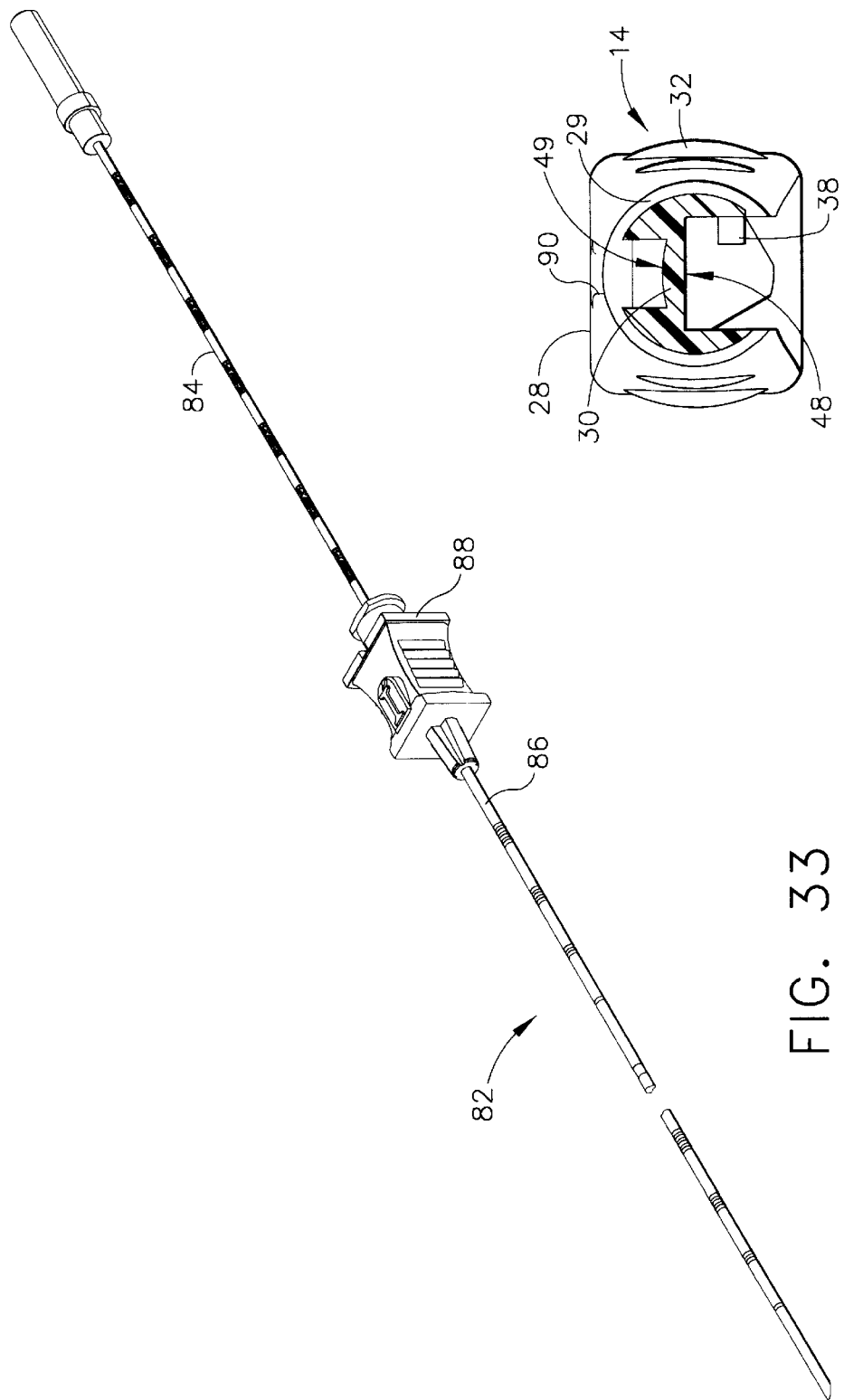

BRACHYTHERAPY SEED CARTRIDGE

This is a Continuation of U.S. patent application Ser. No. 09/359,867 Filed Jul. 26, 1999 now U.S. Pat. No. 6,267,718.

This application is related to the following copending patent applications: U.S. patent application Ser. No. 09/260,705 now U.S. Pat. No. 6,221,003 which is hereby incorporated herein by reference.

FIELD OF THE INVENTION

The present invention relates, in general, to a brachytherapy seed cartridge and, more particularly, to an improved brachytherapy seed cartridge including a removable seed drawer.

BACKGROUND OF THE INVENTION

Prostatic cancer has been estimated to affect as many as one in three men. In the U.S. alone, this implies an estimated fifty-million patients who are candidates for treatment of prostatic cancer. Prior methods of treatment include surgical intervention, external radiotherapy, and other brachytherapy (interstitial radiation) techniques. A general discussion of the localized use of radiation therapy is found in Bagshaw, M. A., Kaplan, I. D. and Cox, R. C., Radiation Therapy for Localized Disease, CANCER 71: 939–952, 1993. Disadvantages associated with surgical intervention include impotence and incontinence. External radiotherapy may have deleterious effects on surrounding normal tissues (e.g., the bladder, the rectum, and the urethra). In contrast, brachytherapy diminishes complications such as impotence and incontinence, and allows a higher and more concentrated radiation dose to be delivered to the prostate gland as compared to external radiotherapy. An additional advantage of brachytherapy is that treatment can be accomplished within a matter of days as compared to weeks, greatly reducing radiation exposure of the adjacent organs.

Prostate brachytherapy can be divided into two categories, based upon the radiation level used. The first category is temporary implantation, which uses high activity sources, and the second category is permanent implantation, which uses lower activity sources. These two techniques are described in Porter, A. T. and Forman, J. D., Prostate Brachytherapy, CANCER 71: 953–958, 1993. The predominant radioactive sources used in prostate brachytherapy include iodine-125, palladium-103, gold-198, ytterbium-169, and iridium-192. Prostate brachytherapy can also be categorized based upon the method by which the radioactive material is introduced into the prostate. For example, a open or closed procedure can be performed via a suprapubic, transperineal or retropubic approach.

While there are various therapies to treat this condition, one of the more successful approaches is to expose the prostate gland to radiation by implanting radioactive seeds. The seeds are implanted in rows and are carefully spaced to match the specific geometry of the patient's prostate gland and to assure adequate radiation dosages to the tissue. Current techniques to implant these seeds include loading them one at a time into the cannula of a needle-like insertion device, which may be referred to as a brachytherapy needle. Between each seed may be placed a spacer, which may be made of catgut. In this procedure, a separate brachytherapy needle is loaded for each row of seeds to be implanted.

In brachytherapy procedures, large amounts of time are currently consumed loading radio active seeds and spacers into the brachytherapy needles. Further, once the needles are loaded, it becomes difficult to verify the dosage (i.e. number of seeds) or to check the level of radioactivity in any individual seed or seeds. Thus, it is preferable to load the appropriate number of seeds and spacers into a cartridge which may then be used to visually verify the number of seeds or to conveniently extract one or more seeds to verify the radio activity of the seeds prior to loading the seeds into a brachytherapy needle. It is also preferable, in certain circumstances, to sterilize the seeds prior to loading them into the brachytherapy needles, allowing the surgeon to review the dosage after sterilization and immediately prior to implantation.

It would, therefore, be advantageous to design a brachytherapy seed cartridge which decreases the time required to check dosage and radioactivity. It would further be advantageous to design a brachytherapy seed cartridge which facilitates loading of brachytherapy needles prior to the brachytherapy procedure. In particular, it would be advantageous to design a brachytherapy seed cartridge which is adapted to organize, view and conveniently add or remove seeds and spacers.

SUMMARY OF THE INVENTION

The present invention is directed to a seed cartridge assembly including a cartridge body, a seed drawer slideably disposed within the cartridge body, a radiation shield slideably disposed around the cartridge body and a seed retainer in the seed drawer. Further embodiments of the present invention include a seed cartridge assembly as described above including a gravity lock between the seed drawer and the cartridge body. Further embodiments of the present invention include a seed cartridge assembly as described above, wherein the cartridge body includes a magnification lens positioned above the seed drawer. Further embodiments of the present invention include a seed cartridge assembly as described above wherein a seed channel extends axially along the seed drawer and a plurality of vents extending from the seed channel to an exterior surface of the seed drawer. Further embodiments of the present invention include a seed cartridge assembly as described above wherein the gravity lock includes a moveable locking element, a first locking recess in an interior surface of the cartridge body and a second locking recess in an exterior surface of the drawer opposite the first locking recess.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is a plan view of the body of a seed cartridge according to the present invention.

FIG. 4 is a side elevation view of the seed cartridge body illustrated in FIG. 3.

FIG. 5 is a bottom view of the seed cartridge body illustrated in FIG. 3.

FIG. 6 is an enlarged distal end view of the seed cartridge body taken along line 6—6 of FIG. 4.

FIG. 7 is an enlarged proximal end view of the seed cartridge body taken along line 7—7 of FIG. 4.

FIG. 8 is an enlarged view in upright section of the seed cartridge body taken along line 8—8 of FIG. 4.

FIG. 9 is an enlarged view in upright section of the seed cartridge body taken along line 9—9 of FIG. 4.

FIG. 10 is an upright section view of the seed cartridge body taken along line 10—10 of FIG. 3.

FIG. 11 is a plan view of the seed drawer of the seed cartridge illustrated in FIG. 2.

FIG. 12 is a side elevation view of the seed drawer illustrated in FIG. 11.

FIG. 13 is a bottom view of the seed drawer illustrated in FIG. 11.

FIG. 14 is an enlarged proximal end view taken along line 14—14 of FIG. 12.

FIG. 15 is an enlarged view in upright section taken along line 15—15 of FIG. 12.

FIG. 16 is an upright section view taken along line 16—16 of FIG. 11.

FIG. 20 is a plan view of a seed cartridge assembly seed retainer according to the present invention.

FIG. 21 is a side elevational view of the seed retainer illustrated in FIG. 20.

FIG. 22 is an enlarged plan view of a seed cartridge assembly locking cylinder according to the present invention.

FIG. 26 is an isometric view of a seed cartridge according to the present invention wherein seeds and spacers are positioned for loading into the seed cartridge drawer.

FIG. 27 is an isometric view of a body and drawer of a loaded seed cartridge according to the present invention wherein the seed cartridge drawer has been closed.

FIG. 28 is an isometric view of a loaded seed cartridge assembly according to the present invention wherein the radiation shield is closed.

FIG. 29 is an isometric view of a loaded seed cartridge assembly with the seed cartridge drawer opened for the removal of one or more seeds.

FIG. 33 is an isometric view of a loaded brachytherapy needle in combination with its stylet.

FIG. 34 is an enlarged view in upright section of the seed cartridge body taken along line 34—34 of FIG. 4.

DETAILED DESCRIPTION OF THE INVENTION

Figure 1:
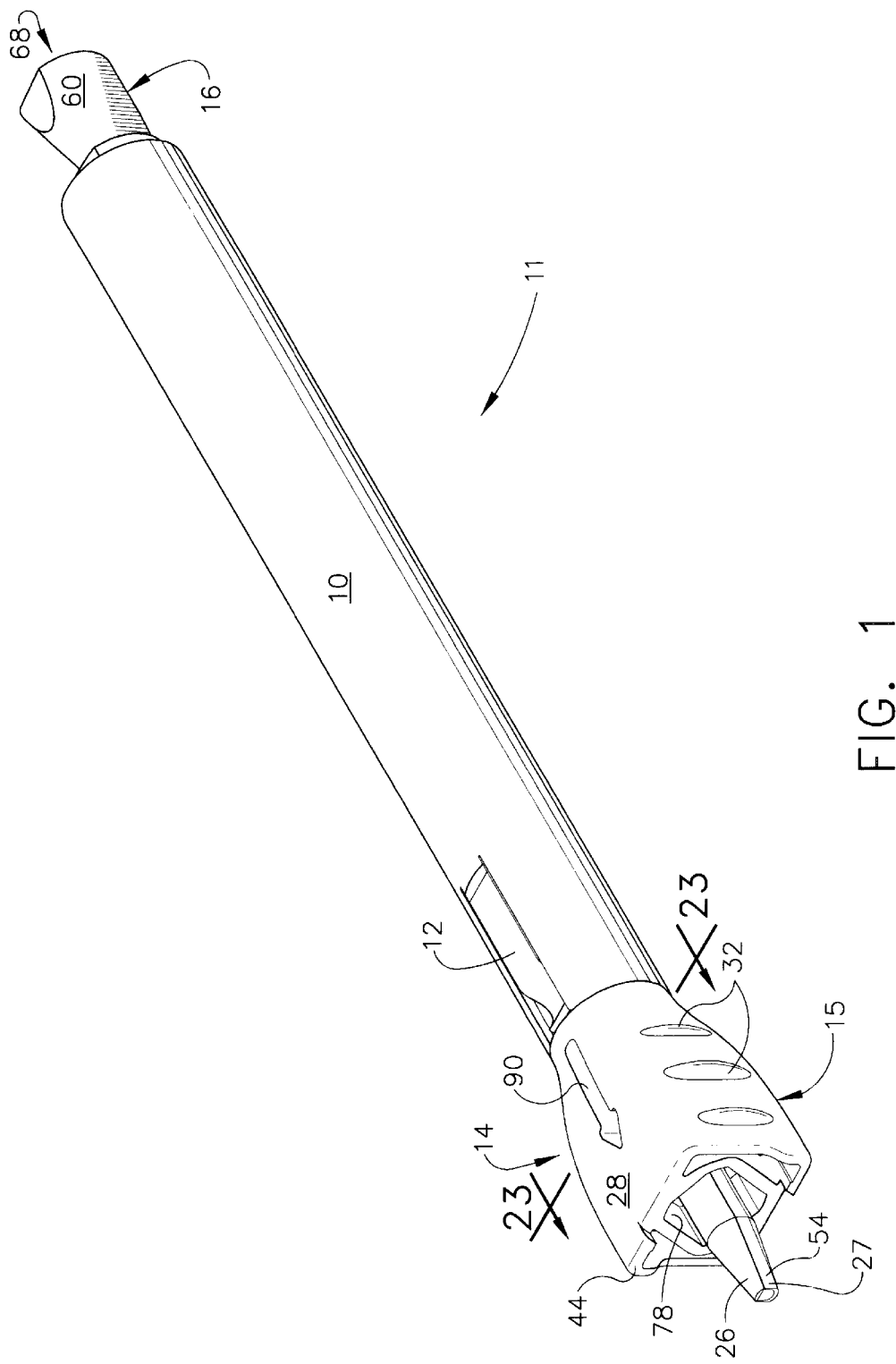
FIG. 1 is a perspective view of a of a seed cartridge assembly according to the present invention, wherein the seed cartridge assembly contains radioactive seeds employed in the treatment of cancer.
Figure 2:
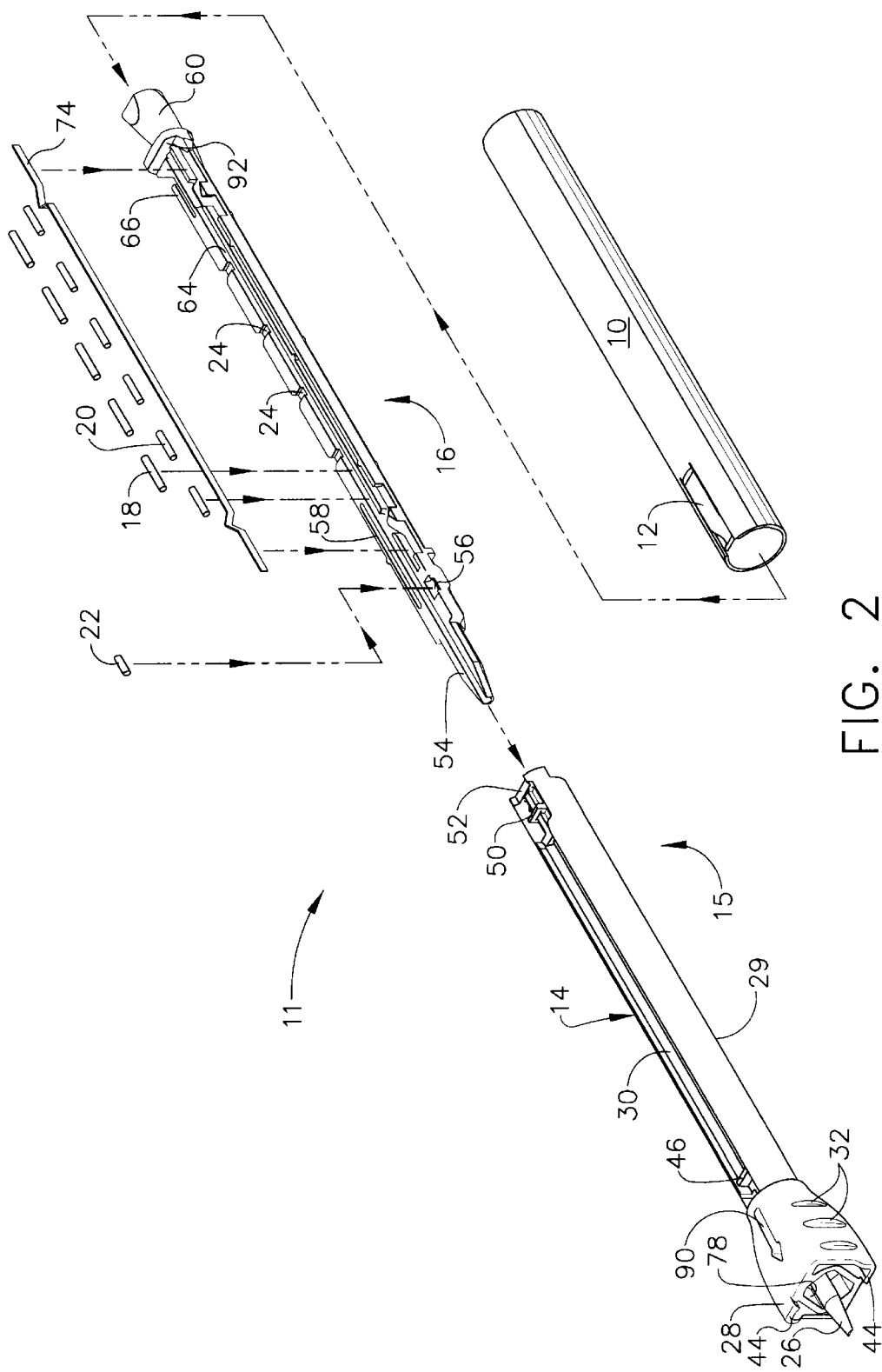
FIG. 2 is an exploded perspective view of the elements of the seed cartridge assembly illustrated in FIG. 1.

FIG. 1 is a perspective view of one embodiment of a seed cartridge assembly 11 according to the present invention. In the embodiment illustrated in FIG. 1, seed cartridge assembly 11 is adapted to hold and dispense radioactive seeds which may be employed in the treatment of, for example, cancerous prostates. As illustrated in FIG. 1, seed cartridge assembly 11 is fully assembled and includes a seed cartridge 15 and a radiation shield 10. Seed cartridge 15 includes a cartridge body 14 and a seed drawer 16. FIG. 2 is an exploded perspective view of the elements of the cartridge assembly FIG. 1, including seed cartridge 15 and radiation shield 10. Cartridge body 14 of seed cartridge 15 includes a cartridge hub 28 and a cartridge shaft 29. Cartridge hub 28 includes an upper needle guide 26, cartridge hub grips 32, hub locking flanges 44, a luer opening 78 and an orientation indicator 90. Cartridge shaft 29 includes a viewing lens 30, a distal shield locking rib 46, an intermediate shield locking rib 50 and a proximal shield locking rib 52. Viewing lens 30 may be, for example, a prism. Seed drawer 16 of seed cartridge 15 includes locking cylinder 22, vents 24, lower needle guide 54, lower locking recess 56, locking spring 58, rear handle 60, seed channel 64, locking nib 66 and seed retainer 74. In FIG. 2, brachytherapy seeds 20 are interspersed with spacers 18. Spacers 18 may be, for example, absorbable spacers made from an autoclaveable material such as, for example a polyglectin 910. With seed drawer 16 positioned in its closed position, upper needle guide 26 and lower needle guide 54 combine to form needle guide 27. Radiation shield 10 of seed cartridge assembly 11 includes a locking tab 12.

FIGS. 3–5 illustrate one embodiment of cartridge body 14. FIG. 3 is a plan view of cartridge body 14. FIG. 4 is a side elevation view of cartridge body 14. FIG. 5 is a bottom view of cartridge body 14. As illustrated in FIG. 5, cartridge body 14 further includes lower drawer support 34, drawer locking spring seat 36, lower drawer support 38, distal retention tab 40, proximal retention tab 42 and an upper locking recess 72.

FIGS. 6–10 are cut away views of one embodiment of the present invention. FIG. 6 is an enlarged end view of cartridge body 14 taken along line 6—6 looking into cartridge hub 28 as illustrated in FIG. 4. FIG. 7 is an enlarged end view of cartridge body 14 taken along line 7—7 looking into cartridge shaft 29 as illustrated in FIG. 4. FIG. 8 is an enlarged view in upright section of cartridge body 14 taken along line 8—8 through cartridge hub 28 as illustrated in FIG. 4. FIG. 9 is an enlarged view in upright section of cartridge body 14 taken along line 9—9 through cartridge hub 28 as illustrated in FIG. 4. FIG. 10 is an upright section view of cartridge body 14 taken along line 10—10 as illustrated in FIG. 3.

FIGS. 11–13 are a series of views of seed drawer 16 according to one embodiment of the present invention. FIG. 11 is a plan view of seed drawer 16. In FIG. 11 seed drawer 16 includes retainer seat nibs 62 and butt plate 92 while locking spring 58 of seed drawer 16 includes locking nib 59. FIG. 12 is a side elevation view of seed drawer 16 including support rib 70. FIG. 13 is a bottom view of seed drawer 16.

FIGS. 14–16 are a series of views, including cutaway views, of one embodiment of the present invention. FIG. 14 is an enlarged proximal end view of seed drawer 16 looking from the proximal to the distal end of seed drawer 16 taken along line 14—14 as illustrated in FIG. 12. FIG. 15 is an enlarged view in upright section looking toward the distal end of seed drawer 16 taken along line 15—15 as illustrated in FIG. 12. FIG. 16 is an upright section view of seed drawer 16 taken along line 16—16 as illustrated in FIG. 11.

Figure 17:
FIG. 17 is a plan view of a seed cartridge radiation shield according to the present invention.
Figure 18:
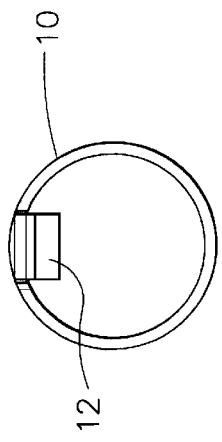
FIG. 18 is an enlarged distal end view in upright disposition of the radiation shield illustrated in FIG. 17.
Figure 19:
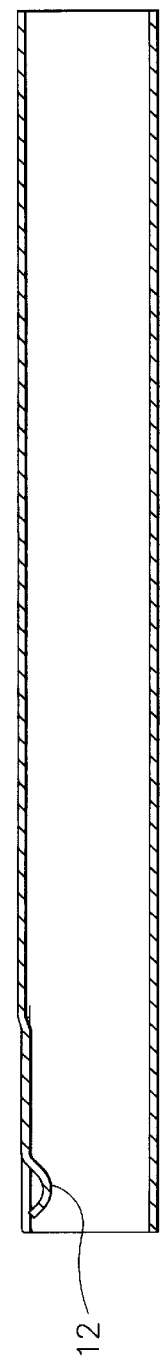
FIG. 19 is a centerline section view of the radiation shield taken along line 19—19 of FIG. 16.

FIGS. 17–19 are a series of views, including a cutaway view of a tubular radiation shield 10 according to the present invention. FIG. 17 is a plan view of radiation shield 10. FIG. 18 is an enlarged distal end view in upright disposition looking into the distal end of radiation shield 10 along line 18—18 as illustrated in FIG. 17. FIG. 19 is a centerline section view of radiation shield 10 taken along line 19—19 as illustrated in FIG. 17.

FIGS. 20 and 21 are side and top views of seed retainer 74 according to the present invention. FIG. 20 is a plan view of seed retainer 74. FIG. 21 is a side elevational view of seed retainer 74. FIG. 22 is an enlarged plan view of a locking cylinder 22 according to one embodiment of the present invention.

Figure 23:
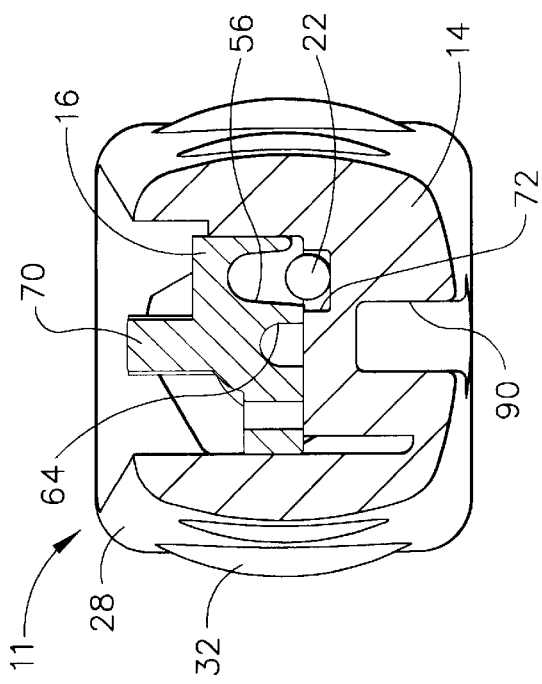
FIG. 23 is an enlarged upright section view through the locking cylinder, seed cartridge body and seed drawer in assembly.
Figure 24:
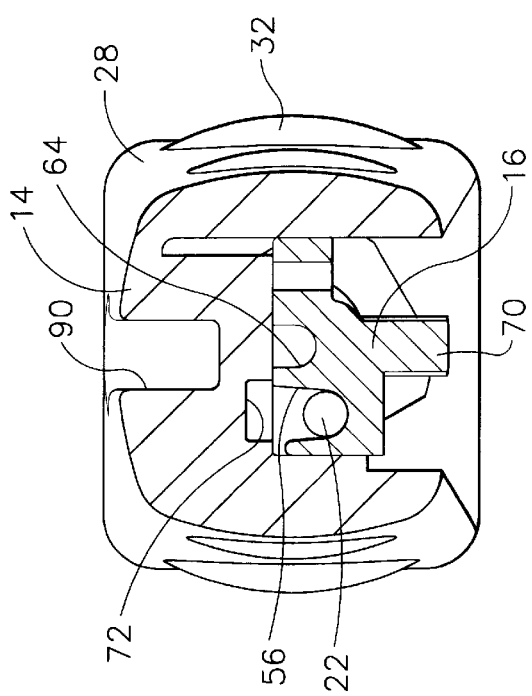
FIG. 24 is an enlarged inverted view of the section view of FIG. 23 illustrating the position of the locking cylinder when the seed cartridge assembly is inverted.

FIGS. 23 and 24 illustrate the interaction of locking cylinder 22 with lower locking recess 56 and upper locking recess 72. FIG. 23 is an enlarged upright section view through locking cylinder 22, cartridge hub 28 and seed drawer 16 of seed cartridge assembly 11 along line 23—23 as illustrated in FIG. 1. FIG. 24 is an enlarged view of the section view of FIG. 23 illustrating the position of locking cylinder 22 in lower locking recess 56 and upper locking recess 72 with cartridge assembly 11 inverted.

Figure 25:
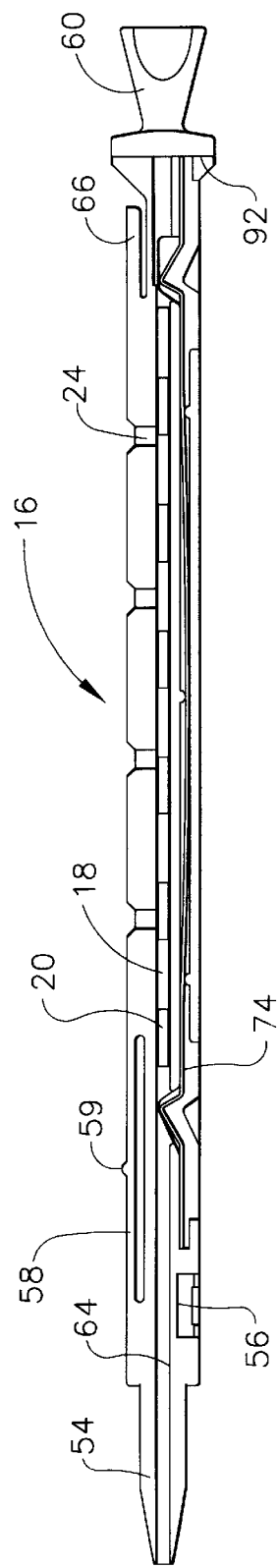
FIG. 25 is a plan view of a seed drawer according to the present invention including a retainer, seeds and spacers.
Figure 30:
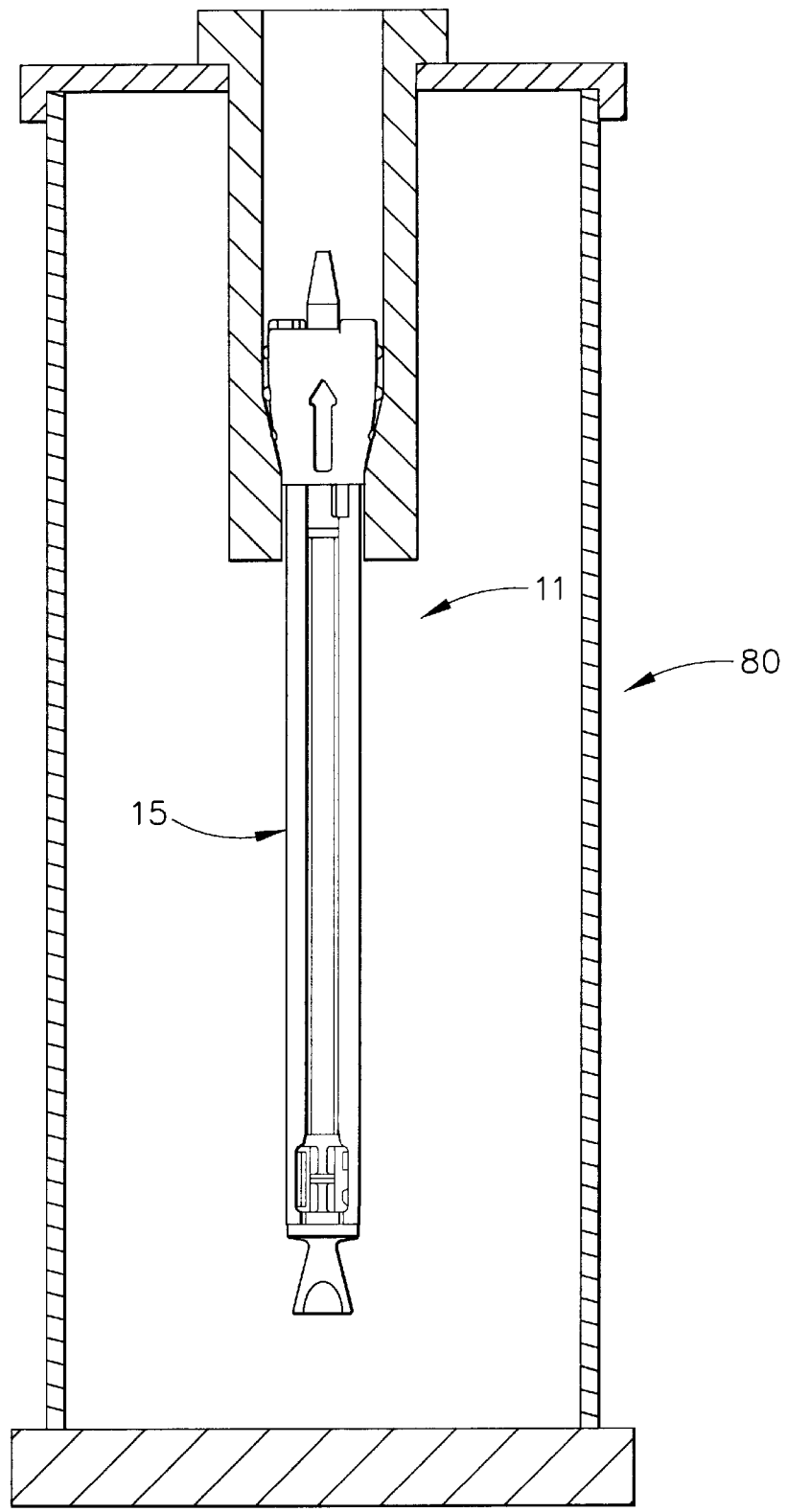
FIG. 30 is a schematic view of a seed cartridge according to the present invention positioned in an assay device.
Figure 31:
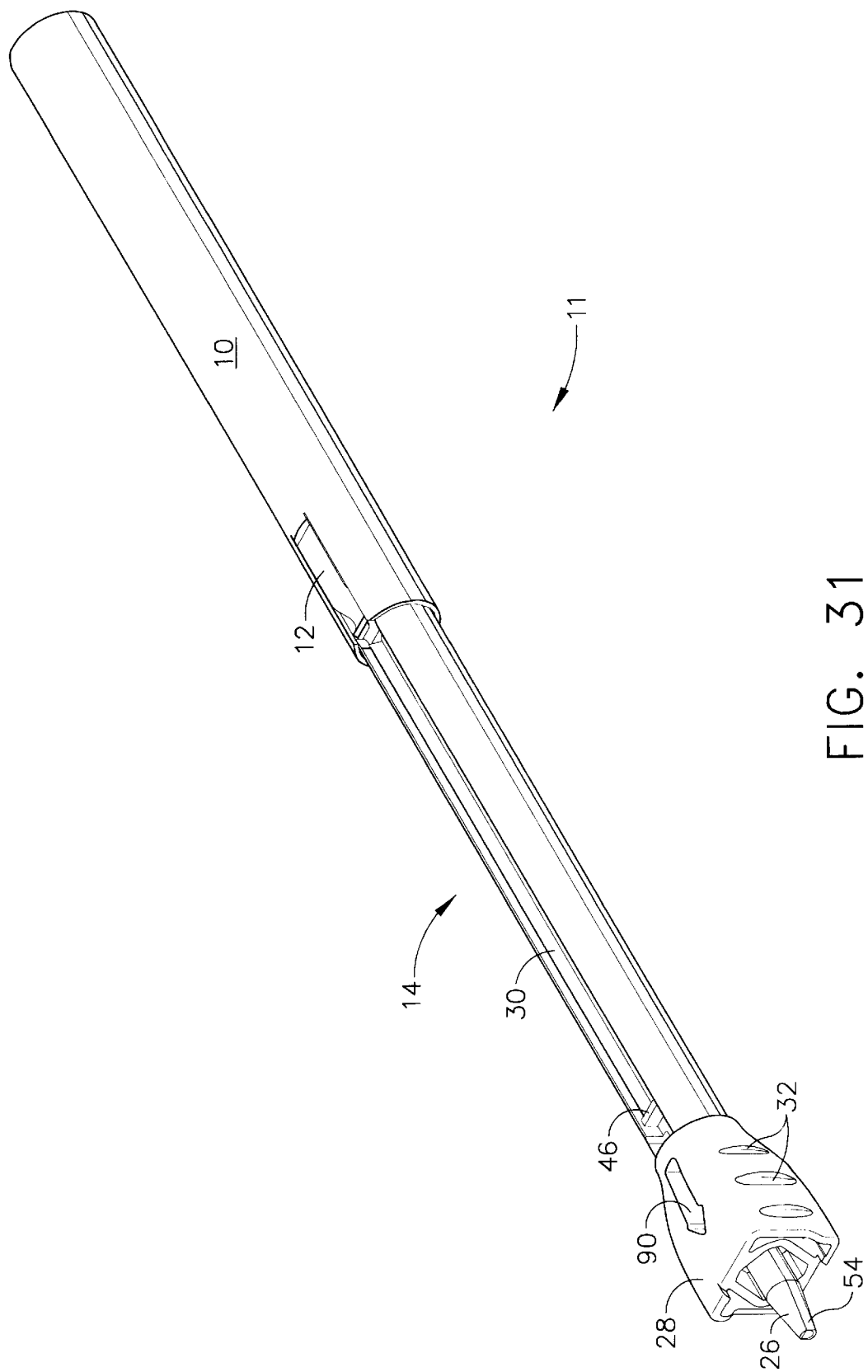
FIG. 31 is an isometric view of a seed cartridge assembly according to the present invention with its radiation shield in an open position.

FIGS. 25–28 illustrate a procedure according to the present invention for loading radioactive seeds into a seed cartridge assembly 11 according to the present invention. FIG. 25 is a plan view of the seed drawer 16 including, spacers 18, brachytherapy seeds 20 and seed retainer 74 in assembly. FIG. 26 is an isometric view of seed cartridge 15 with seed drawer 16 open to receive spacers 18 and brachytherapy seeds 20. Seeds and spacers may be loaded into seed drawer 16 by, for example, hand wearing leaded gloves or using tweezers. FIG. 27 is an isometric view of a loaded seed cartridge 15 according to the present invention after spacers 18 and brachytherapy seeds 20 have been loaded into seed drawer 16 and seed drawer 16 has been closed. The number of seeds 20 and spacers 18 placed in seed drawer 16 will, of course, depend upon the procedure. Viewing lens 30, which may be, for example, a window having a convex outer surface, provides magnification of seeds 20 for easier counting and classification after they are loaded, seed drawer 16 is closed and radiation shield 10 is moved back to expose viewing lens 30. FIG. 28 is an isometric view of a loaded cartridge assembly 11 wherein radiation shield 10 has been added to seed cartridge 15 to substantially reduce radiation emitted to the surrounding environment by brachytherapy seeds 20. FIG. 29 is an isometric view of a cartridge assembly opened by a hospital physicist for the removal of a 10% seed sample for assay purposes. In this assay procedure, radiation shield 10 stays in place and calibration is accomplished one seed at a time. In an alternate procedure, illustrated in FIG. 30, a seed cartridge 15 is inserted in an assay device, since seed cartridge 15 does not include radiation shield 10, the resulting calibration would yield the total count for the contents of seed cartridge 15. FIG. 31 is an isometric view of a cartridge assembly 11 with its radiation shield 10 withdrawn for a visual count of the contents. Radiation shield 10 is retained on the proximal end of seed cartridge 15 by locking tab 12 and locking rib 50.

Figure 32:
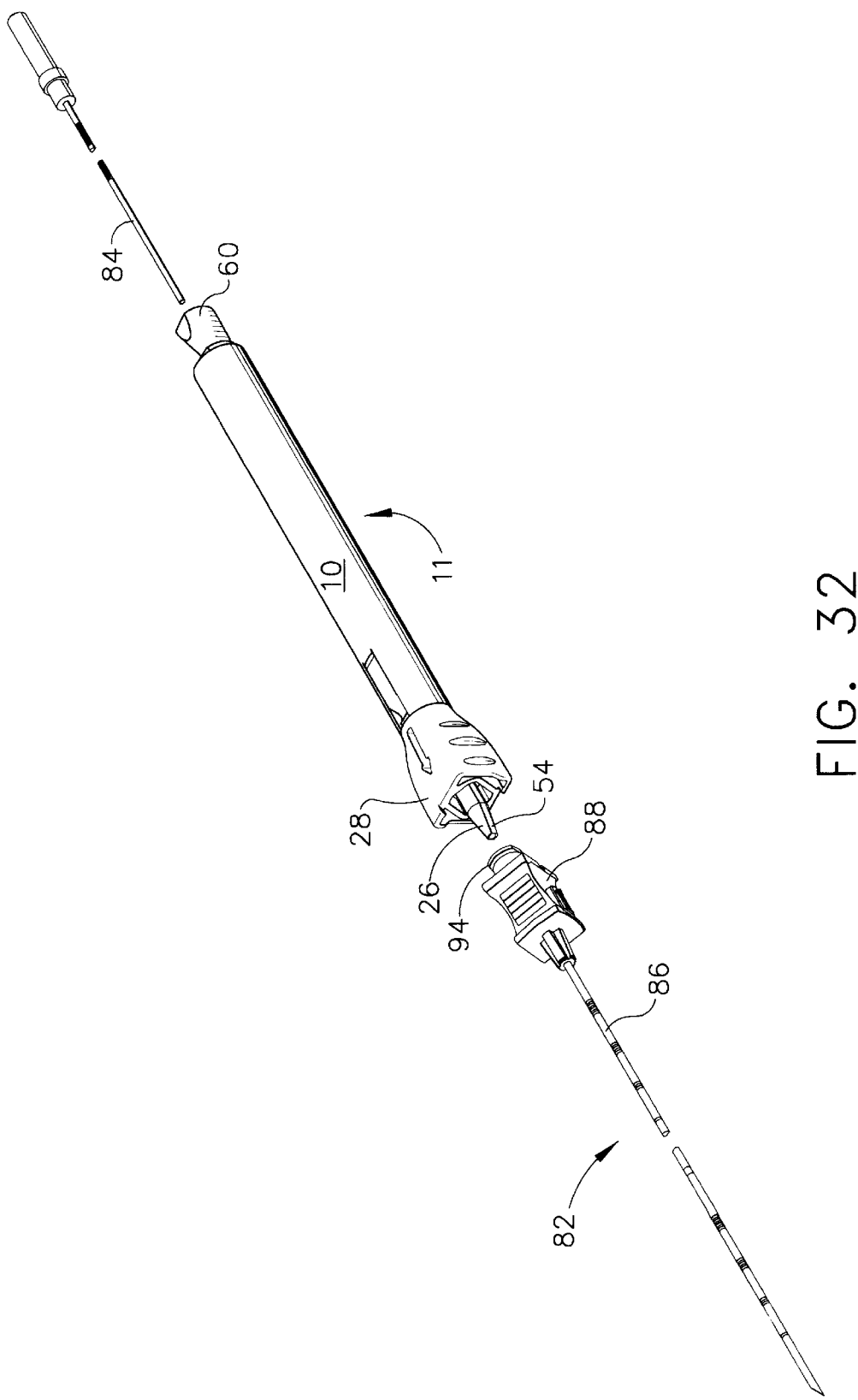
FIG. 32 is an exploded isometric view of a brachytherapy needle and a stylet rod in combination with a seed cartridge assembly according to the present invention.

FIGS. 32 and 33 illustrate how seeds 20 are incorporated into a brachytherapy needle 82. FIG. 32 is an exploded isometric view of a cartridge assembly 11, brachytherapy needle 82, and a stylet 84. In the embodiment illustrated, brachytherapy needle 82 is particularly adapted for use in brachytherapy procedures involving treatment of cancer of the prostate. Suitable brachytherapy needles are available from Indigo Medical, Incorporated as Model BPN18. In the embodiment of the invention illustrated, needle hub 88 of brachytherapy needle 82 may be attached to cartridge hub 28 with a sixty degree turn, locking the proximal end of brachytherapy needle 82 to the distal end of seed cartridge 11. Stylet 84 may then be used to move spacers 18 and seeds 20 from seed cartridge 11 to needle cannula 86. Once spacers 18 and seeds 20 are positioned in needle cannula 86, stylet 84 may be removed. FIG. 33 is an isometric view of a loaded brachytherapy needle 82 with seed cartridge 11 removed and stylet 84 inserted into needle hub 88. Once brachytherapy needle 82 is properly positioned within the patient, stylet 84 may be used to force spacers 18 and seeds 20 out of needle cannula 86 and into the portion of the patient to be treated, such as, for example, the prostate.

FIG. 34 is an enlarged view in upright section of cartridge body 14 taken along line 8—8 through cartridge shaft 29 as illustrated in FIG. 4. In the embodiment of the invention illustrated in FIG. 34, viewing lens 30 includes a convex upper surface 49 and a flat lower surface 48. In the embodiment illustrated, lower surface 48 of viewing lens 30 acts as a channel cover for seed channel 64, holding spacers 18 and seeds 20 in channel 64 when seed drawer 16 is closed. Upper surface 49 of viewing lens 30, being convex magnifies images of elements placed under lower surface 48, thus, viewing the contents of seed channel 64 from the top of seed cartridge 15 through viewing lens 30 makes the contents appear larger and makes it easier for a technician to count the number of seeds and spacers in seed channel 64 and to ensure that the seeds and spacers in seed channel 64 are properly arranged.

Referring now to FIGS. 1–25, there is illustrated one embodiment of the present invention. In FIGS. 1–25, a seeding needle cartridge assembly 11 useful for storing and dispensing radioactive seeds 20 such as those used in low dose brachytherapy procedures is shown. In the embodiment shown and described herein, cartridge assembly 11 includes radiation shield 10, cartridge body 14, and seed drawer 16. Within seed drawer 16 is nestled seed retainer 74 which is adapted to passively enclose the brachytherapy seeds 20 and spacers 18 in seed channel 64 until seeds 20 and spacers 18 are propelled through seed channel 64 and out needle guide 27 by, for example, stylet 84. Seed cartridge 11 further includes luer opening 78 which is adapted to mate with a conventional brachytherapy needle 82 having a conventional luer mating element 94.

As best illustrated in FIGS. 23 and 24 seed cartridge assembly 11 includes a gravity lock which prevents seed drawer 16 from opening when seed cartridge assembly 11 is inverted. Thus, the gravity lock prevents seed drawer 16 from being opened with seed cartridge assembly 11 in a position where seeds 20 would fall out of seed channel 64. In the embodiment of the invention illustrated in FIGS. 23 and 24, the gravity lock includes cylinder 22, lower locking recess 56 and upper locking recess 72 wherein the depth of lower locking recess is greater than the cross-sectional diameter of locking cylinder 22 while the depth of upper locking recess is less than the diameter of locking cylinder 22. Thus, with seed cartridge assembly in an upright position, as illustrated in FIG. 23, the force of gravity displaces locking cylinder 22 toward seed drawer 16 and locking cylinder 22 sits in lower locking recess 56, leaving seed drawer 16 free to slide in and out of cartridge body 14. However, with seed cartridge assembly 11 in an inverted position, as illustrated in FIG. 24, the force of gravity displaces locking cylinder 22 toward cartridge body 14 such that a portion of locking cylinder 22 rests in upper locking recess 72 and a portion of locking cylinder 22 extends into lower locking recess 56. In the inverted position, as illustrated in FIG. 24, cartridge drawer 16 will not freely slide in and out of cartridge body 14 because locking cylinder 22 obstructs the movement of cartridge drawer 16 with respect to cartridge body 14. In particular, when seed cartridge assembly 11 is inverted, as illustrated in FIG. 24, and force is applied to attempt to move seed drawer 16 proximally with respect to seed cartridge body 14 (i.e. to open seed drawer 16) the proximal end of locking cylinder 22 is forced against the proximal end of upper locking recess 72 while the distal end of locking cylinder 22 is forced against the distal end of lower locking recess 56, preventing seed drawer 16 from moving proximally with respect to cartridge body 14.

Referring now to FIGS. 3–10, the cartridge body 14 is constructed to have a transparent or translucent viewing lens 30, which is designed to be of a convex structure so as to magnify contents beneath viewing lens 30. Lower drawer support 34, lower drawer support 38 and retention tabs 40 and 42 provide a flat base on which seed drawer 16 can slide and rest. Drawer locking spring seat 36 is adapted to engage locking nib 59 with seed drawer 16 closed. Retention tab 42 is adapted to engage locking nib 66 with seed drawer 16 closed and to engage locking nib 59 with seed drawer 16 fully open. Locking tab 96 is adapted to stop against lower drawer support 38 and so inhibit the movement of locking nib 59 past proximal retention tab 42 when seed drawer 16 is opened. Locking spring 58 and locking nib 59 also provide lateral support for seed drawer 16, limiting side to side movement of seed drawer 16 in cartridge body 14.

Cartridge body 14 also includes the cartridge hub 28 which is attached to brachytherapy needle 82 when seeds 20 are to be loaded into needle cannula 86. Cartridge hub grips 32 facilitate gripping cartridge hub 28 for attachment to a needle hub 88. Cartridge hub 28 further includes hub locking flanges 44 which prevent over-rotation of needle hub 88 during attachment. Hub locking flanges 44 may also provide tactile feedback, indicating a fully locked position.

Distal shield locking rib 46, intermediate shield locking rib 50, and proximal shield locking rib 52 are designed to facilitate the positioning, removal and replacement of radiation shield 10 on seed cartridge 15. Distal shield locking rib 46, intermediate shield locking rib 50, and proximal shield locking rib 52 define three different detent positions with which locking tab 12 of radiation shield 10 can rest, with each position revealing different portions of seed cartridge 15.

Referring now to FIGS. 11–16, seed drawer 16 is more explicitly illustrated and labeled. Locking spring 58 along with locking nib 59 mates with drawer locking spring seat 36 in the cartridge body 14 to provide a locking mechanism for the seed drawer 16 within the cartridge body 14. Locking nib 66 also provides resistance which prevents seed drawer 16 from opening accidentally. A sufficiently large force is thus required to overcome the spring and thus deflect the locking spring 58 and locking nib 66, promoting motion of drawer 16 with respect to body 14.

Vents 24 allow steam to enter and leave seed channel 64 in order to sterilize seeds and spacers positioned in seed channel 64 using, for example, an autoclave. Multiple vents 24 are used to ensure that steam can flow freely around spacers 18 and seeds 20 positioned in seed channel 64. Thus, both the seed cartridge assembly 11 and the contents of seed drawer 16 may be sterilized together, after seed drawer 16 has been filled with seeds and spacers. Generally retainer gates 76 of seed retainer 74 prevent spacers 18 and seeds 20 positioned in seed channel 64 from sliding out the proximal or distal ends of seed cartridge assembly. Retainer seat nibs 62 hold seed retainer 74 in place through the application of a three point bending force, limiting proximal-distal motion and lateral motion of seed retainer 74 when stylet 84 is inserted into seed channel 64 to force spacers 18 and seeds 20 out the distal end of needle guide 27. As stylet 84 is inserted into seed channel 64, it forces the retainer gate 76 at the proximal end of seed retainer 74 aside and, as it continues to move toward the distal end of seed channel 64, it pushes spacers 18 and seeds 20 past the retainer gate 76 at the distal end of seed retainer 74 and out the distal end of needle guide 27.

Rear handle 60 may be used to open and close seed drawer 16 or to hold seed drawer 16 when it is removed from cartridge body 14. Support rib 70 provides support for the seed drawer 16 in addition to facilitating manufacture and assembly of seed drawer 16 and cartridge body 14. Butt plate 92 provides a stopping point where seed drawer 16 cannot further travel distally relative to cartridge body 14. Rear funnel 68 facilitates insertion of stylet 84 into seed channel 64 in seed cartridge assembly 11.

FIG. 25 demonstrates a typical setup of the seed drawer 16, with brachytherapy seeds 20 and spacers 18 within the retainer gates 76 in seed channel 64. FIGS. 26–33 then demonstrate a typical mode of use. FIG. 26 demonstrates the loading of the brachytherapy seeds 20 and spacers 18 into the seed drawer 16 (specifically in the seed channel 64). Following loading, the seed drawer 16 is inserted into the cartridge body 14. This cartridge is then covered by radiation shield 10 and delivered to the customer, such as, for example, a hospital. Upon receipt, technicians at the hospital may withdraw seed drawer 16 and remove a number of brachytherapy seeds 20 for assay (typically they will remove 10% of all seeds in a batch to calibrate radioactivity). An alternate method of assay is shown in FIG. 30, which illustrates a seed cartridge 15 suspended within an ion chamber 80 (where the method of suspension can be any method of the like where seed cartridge 15 is exposed inside the ion chamber 80). After determining the radioactivity of the brachytherapy seeds 20 and verifying the correct values, radiation shield 10 is repositioned on seed cartridge 15 and seed cartridge assembly 11 is autoclaved alone or with other seed cartridge assemblies.

After the seed cartridge assembly 11 is autoclaved, a number of seed cartridge assemblies 11 (typically 20–25) are matched with the brachytherapy procedure plan and the seeds 20 and spacers 18 are transferred to needle cannulas 86 of brachytherapy needles 82. In particular, for each autoclaved seed cartridge assembly, radiation shield 10 is moved proximally to allow a technician to view the contents of seed channel 64 through the cartridge body 14 in order to identify the order and number of brachytherapy seeds 20 and spacers 18 as shown in FIG. 31. In one embodiment of the present invention, this process is particularly facilitated by the presence of viewing lens 30 above seed drawer 16. The technician then compares the contents of the seed cartridge assembly 11 with a predetermined plan. If the contents of seed drawer 16 do not correspond to the plan, seed drawer 16 may opened as illustrated in FIG. 29 and seeds 20 removed or added to seed drawer 16. If the contents of the seed cartridge assembly match the predetermined plan the seed cartridge assembly 11 is attached to a brachytherapy needle 82. More particularly, luer mating element 94 at the proximal end of needle hub 88 is inserted into luer opening 78 at the distal end of cartridge hub 28. Following attachment, a stylet 84 is used to propel the contents of the seed cartridge assembly 11 through the seed channel 64 into needle cannula 86. Seed cartridge assembly 11 is then disconnected from brachytherapy needle 82 and stylet 84 is positioned in brachytherapy needle 82 to be used intraoperatively as in a normal brachytherapy procedure utilizing preloaded needles.

It will be recognized that equivalent structures may be substituted for the structures illustrated and described herein and that the described embodiment of the invention is not the only structure which may be employed to implement the claimed invention. As one example of an equivalent structure which may be used to implement the present invention, seed channel 64 may be built into cartridge body 14 and accessed using, for example, a living hinge built into seed body 14.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A seed cartridge assembly comprising:
   a cartridge body;
   a seed drawer slideably disposed within said cartridge body;
   a radiation shield slideably disposed around said cartridge body; and
   a seed retainer in said seed drawer,
   wherein the seed cartridge assembly can be autoclaved without destroying the assembly's dimensions and said cartridge body includes a transparent or translucent viewing lens.

2. A seed cartridge assembly according to claim 1, wherein said lens is positioned above said seed drawer and is capable of magnifying the contents of said seed drawer.

3. A seed cartridge assembly according to claim 2, wherein said lens comprises a substantially flat inner surface and a substantially convex outer surface.

4. A seed cartridge assembly according to claim 1, wherein said seed drawer comprises:
   a seed channel extending axially along said seed drawer from a proximal end of said seed drawer to a distal end of said seed drawer; and
   a plurality of vents extending from said seed channel to an exterior surface of said seed drawer.

5. A seed cartridge assembly according to claim 4, wherein said seed retainer comprises:
   a first deflection element positioned at a proximal end of said seed channel, said first deflection element substantially blocking said channel, wherein said first deflection element comprises:
      a first ramped surface at a proximal end of said first deflection element, wherein said first ramped surface is positioned at an angle of approximately thirty degrees with respect to at least one wall of said seed channel;
      a first square surface at a distal end of said first deflection element, wherein said first square surface is positioned at an angle of approximately ninety degrees with respect to one wall of said seed channel;
   a second deflection element positioned at a distal end of said seed channel, said second deflection element substantially blocking said channel, wherein said second deflection element comprises;
      a second ramped surface at a distal end of said second deflection element, wherein said second ramped surface is positioned at an angle of approximately thirty degrees with respect to said one wall of said seed channel;
      a first square surface at a proximal end of said second deflection element, wherein said second square surface is positioned at an angle of approximately ninety degrees with respect to said one wall of said seed channel.

6. A seed cartridge assembly according to claim 1, wherein said seed cartridge further comprises a gravity lock between said seed drawer and said cartridge body, wherein said gravity lock comprises:
   a moveable locking element;
   a first locking recess in an interior surface of said cartridge body said moveable element being positioned in said first locking recess when said seed cartridge assembly is in an inverted position wherein a portion of said moveable element protrudes from said first locking recess when said seed cartridge assembly is in said inverted position;
   a second locking recess in an exterior surface of said drawer opposite said first locking recess, said removable element being positioned fully within said second locking recess when said seed cartridge assembly is in an upright position.

7. A seed cartridge assembly according to claim 6, wherein said locking element comprises a cylinder.

8. A seed cartridge assembly according to claim 7, wherein said first locking recess has a depth which is less than the diameter of said cylinder; and
   said second locking recess has a depth which is greater than the diameter of said cylinder.

9. A seed cartridge assembly according to claim 1, wherein said seed cartridge assembly includes a luer opening at a distal end thereof, said opening including a plurality of stops positioned at an angle of approximately sixty degrees with respect to one axis of said luer opening.

10. A seed cartridge assembly according to claim 1, wherein said seed cartridge further includes a plurality of brachytherapy seeds positioned in said seed drawer.

11. A seed cartridge assembly comprising:
   a cartridge body;
   a seed drawer slideably disposed within said cartridge body;
   a seed channel extending axially along said seed drawer from a proximal end of said seed drawer to a distal end of said seed drawer;
   a plurality of vents extending from said seed channel to an exterior surface of said seed drawer; and
   a seed retainer in said seed drawer.

12. A seed cartridge assembly according to claim 11, wherein said cartridge body includes a magnification lens positioned above said seed drawer.

13. A seed cartridge assembly according to claim 12, wherein said magnification lens comprises a substantially flat inner surface and a substantially convex outer surface.

14. A seed cartridge assembly according to claim 13, wherein said seed drawer comprises:
- a radiation shield slideably disposed within said cartridge body; and
- a handle at said proximal end of said seed drawer.

15. A seed cartridge assembly according to claim 14, wherein said seed retainer comprises:
- a first deflection element positioned at a proximal end of said seed channel, said first deflection element substantially blocking said channel, wherein said first deflection element comprises:
  - a first ramped surface at a proximal end of said first deflection element, wherein said first ramped surface is positioned at an angle of approximately thirty degrees with respect to at least one wall of said seed channel;
  - a first square surface at a distal end of said first deflection element, wherein said first square surface is positioned at an angle of approximately sixty degrees with respect to one wall of said seed channel;
- a second deflection element positioned at a distal end of said seed channel, said second deflection element substantially blocking said channel, wherein said second deflection element comprises;
  - a second ramped surface at a distal end of said second deflection element, wherein said second ramped surface is positioned at an angle of approximately thirty degrees with respect to said one wall of said seed channel;
  - a first square surface at a proximal end of said second deflection element, wherein said second square surface is positioned at an angle of approximately sixty degrees with respect to said one wall of said seed channel.

16. A seed cartridge assembly according to claim 11, wherein said seed cartridge further comprises a gravity lock between said seed drawer and said cartridge body, wherein said gravity lock comprises:
- a moveable locking element;
- a first locking recess in an interior surface of said cartridge body said moveable element being positioned partially in said first locking recess when said seed cartridge assembly is in an inverted position wherein a portion of said moveable element protrudes from said first locking recess when said seed cartridge assembly is in said inverted position;
- a second locking recess in an exterior surface of said drawer opposite said first locking recess, said removable element being positioned fully within said second locking recess when said seed cartridge assembly is in an upright position.

17. A seed cartridge assembly according to claim 16, wherein said locking element comprises a cylinder.

18. A seed cartridge assembly according to claim 17, wherein said first locking recess has a depth which is less than the diameter of said cylinder; and
  said second locking recess has a depth which is greater than the diameter of said cylinder.

19. A seed cartridge assembly according to claim 11, wherein said seed cartridge assembly includes a luer opening at a distal end thereof, said opening including a plurality of stops positioned at an angle of approximately sixty degrees with respect to one axis of said luer opening.

20. A seed cartridge assembly according to claim 11, wherein said seed cartridge further includes a plurality of brachytherapy seeds positioned in said seed drawer.

* * * * *